| United States Patent [19] | [11] Patent Number: 5,074,902 |
|---|---|
| Connick, Jr. et al. | [45] Date of Patent: Dec. 24, 1991 |

[54] GRANULAR PRODUCTS CONTAINING FUNGI ENCAPSULATED IN A WHEAT GLUTEN MATRIX FOR BIOLOGICAL CONTROL OF WEEDS

[76] Inventors: William J. Connick, Jr., 4936 Louisa Dr., New Orleans, La. 70126; Clyde D. Boyette, 301 N. W. Deer Creek Dr., Leland, Miss. 38756

[21] Appl. No.: 560,791

[22] Filed: Jul. 30, 1990

[51] Int. Cl.$^5$ ............... A01N 63/04; A01N 25/12
[52] U.S. Cl. .................................. 71/79; 71/DIG. 1; 424/93
[58] Field of Search ............... 71/79, DIG. 1; 424/93

[56] References Cited

U.S. PATENT DOCUMENTS

| 3,137,631 | 6/1964 | Soloway | 167/83 |
|---|---|---|---|
| 3,780,195 | 12/1973 | Balassa | 426/350 |
| 4,230,687 | 10/1980 | Sair et al. | 424/22 |
| 4,668,512 | 5/1987 | Lewis et al. | 424/93 |
| 4,718,935 | 1/1988 | Walker et al. | 71/79 |
| 4,724,147 | 2/1988 | Marois et al. | 424/93 |
| 4,775,405 | 10/1988 | Caulder et al. | 71/79 |
| 4,798,786 | 1/1989 | Tice et al. | 435/177 |
| 4,859,377 | 8/1989 | Shasha et al. | 264/4.1 |
| 4,902,333 | 2/1990 | Quimby | 71/79 |

FOREIGN PATENT DOCUMENTS 226394 6/1987 European Pat. Off. .
63-251053 2/1989 Japan .

OTHER PUBLICATIONS

Walker et al., (1983) "Sodium Alginate for Production and Formulation at Mycoherbicides", *Weed Science*, 1983, 31:333-338.
Boyette "Evaluation of *Alternaria crassg* for biological control of Jinson weed . . . ", *Plant Science* 45:223-228, 1986.
Templeton et al., "Progress and Potentical of Weed Control with Mycoherbicides", *Reviews of Weed Science*, vol. 2, 1-14, 1986.

*Primary Examiner*—Richard L. Raymond
*Assistant Examiner*—S. Mark Clardy

[57] ABSTRACT

Weed pathogenic fungi to be encapsulated in a wheat gluten matrix are blended with flour and water to make a cohesive dough. The dough is extruded, rolled out into a sheet, or otherwise shaped, and dried to form products that contain the fungi entrapped throughout the gluten matrix. The encapsulated fungi grow onto the surface of said products when provided with sufficient light and water. The products of this invention may be used to infect and kill weeds.

17 Claims, No Drawings

GRANULAR PRODUCTS CONTAINING FUNGI ENCAPSULATED IN A WHEAT GLUTEN MATRIX FOR BIOLOGICAL CONTROL OF WEEDS

BACKGROUND OF THE INVENTION

1. Field of the Invention

This invention relates to a novel method of encapsulation of weed pathogenic fungi in products having a wheat gluten matrix, the compositions prepared thereby, and their use for the biological control of weeds.

2. Description of the Prior Art

Encapsulation of living biological control agents is a promising means of formulating these organisms into effective products for use against agricultural pests. Biological control using living natural enemies of pests is distinguished from control by the use of chemical pesticides. When encapsulated or entrapped in a solid matrix, delicate biological control organisms (agents) are sheltered from rapid desiccation, microbial competition, and other adverse environmental factors which can limit their practical utility.

Encapsulation techniques for incorporating biological control fungi in an alginate matrix have been widely used. In U.S. Pat. No. 4,718,935, Walker et al. disclose the encapsulation of fungi in alginate gel pellets for the control of weeds. In U.S. Pat. No. 4,724,147, Marois et al. disclose the encapsulation of fungi in alginate pellets for control of soilborne plant diseases. In U.S. Pat. No. 4,668,512, Lewis et al. disclose the preparation of alginate pellets that contain wheat bran as nutrient for encapsulated fungi, said pellets used for the control of soilborne plant pathogens. In each of the alginate-based methods referenced above, a fungus was added to a sodium alginate solution that also contained fillers/adjuvants, and the mixture was added dropwise into a $CaCl_2$ solution which reacts with the alginate to transform the droplets into alginate gel pellets containing the fungus. None of the referenced alginate-based patents teach the use of a wheat gluten matrix to encapsulate weed pathogenic fungi.

Biocontrol agents have also been incorporated into a starch matrix. In U.S. Pat. No. 4,859,377, Shasha et al. disclose the encapsulation of entomopathogenic biocontrol agents by blending the agents into an aqueous dispersion of amylose-containing, pregelatinized starch in which reassociation of amylose molecules occurs upon dispersion in an aqueous system causing an insolubilization of the starch matrix. Shasha et al. do not teach the use of a wheat gluten matrix to encapsulate weed pathogenic fungi.

Wheat flour has been used as a nutrient in formulations that contain fungi, but not as a source of gluten to provide cohesiveness and a matrix structure for encapsulation of weed pathogenic fungi. In EP 226394, McCabe et al. disclose the production of microbial inoculants for agricultural uses. Wheat flour is disclosed as a preferred nutrient for fungal cultures, but not as a source of gluten to encapsulate weed pathogenic fungi.

SUMMARY OF THE INVENTION

We have discovered a method of encapsulating or entrapping plant pathogenic fungi, sometimes referred to as mycoherbicides or bioherbicides, in a matrix of dried wheat flour dough where wheat gluten proteins provide the main structural framework. A fungus that is able to control or kill a weed, water, and wheat flour are blended to form a cohesive dough which is rolled out into a sheet, dried, and broken up or ground into granules of the desired size. The fungus becomes incorporated throughout the granule matrix and will grow onto the surface of the granules after application to a suitable environment. Compositions prepared by the practice of this invention can be used to kill weeds.

In accordance with this discovery, it is an object of this invention to provide a facile, gentle, industrially acceptable method of encapsulating delicate, living plant pathogenic fungi into granules, or into structural units of other desirable shapes and sizes.

Another object of this invention is to provide products that are safe for handling, stable in storage, and readily biodegradable in the environment.

It is also an object of the invention that the primary matrix-forming material be derived from natural, renewable agricultural resources.

Another object of this invention is that the method is characterized by good survivability of the entrapped fungi, and versatile so that a wide variety of fillers and adjuvants can easily be incorporated to improve the processing, storage, fungal viability, and efficacy of the final products.

It is also an object of this invention to provide compositions for the biological control of weeds in agricultural fields, gardens, greenhouses, roadsides, utility right-of-way, and aquatic environments.

Other objects and advantages of this invention will become readily apparent from the ensuing description.

DETAILED DESCRIPTION OF THE INVENTION

Wheat flour is a relatively inexpensive agricultural product that is available worldwide, principally for use in food products. When wheat flour is mixed with water at a ratio of about 1:0.6, a cohesive dough is formed. Gluten proteins from the wheat flour provide the main structural matrix of the dough. Any wheat flour with a sufficient amount of protein to form a cohesive dough, usually about 8-18% protein, may be used in the practice of this invention. Semolina, a coarse flour made from durum wheat, is preferred. Semolina's excellent dough-forming properties have made it the flour of choice in preparing alimentary pastes such as macaroni and spaghetti (pasta products). An example of wheat flour used in the practice of this invention is DaVinci brand semolina (distributed by Reese Finer Foods, Inc., Dayton, Ohio 45449, U.S.A.) made from durum wheat.

The fungi contemplated for use herein include all fungi that are pathogenic toward weeds. To demonstrate the flexibility of the method of this invention, each of five weed pathogens was cultured and encapsulated separately.

*Alternaria cassiae* Jurair and Khan, a pathogen of the weeds sicklepod, coffee senna, and showy crotalaria, is on deposit with the Agricultural Research Service Culture Collection (NRRL) in Peoria, Ill., and has accession number NRRL #12553. The address of the Agricultural Research Culture Collection is: A. J. Lyons, Curator, ARS Patent Collection, Culture Collection Research, NRRC, 1815 N. University St., Peoria, Ill. 61604, U.S.A.

*Alternaria crassa*, a pathogen of jimsonweed, is on deposit as NRRL #18136.

*Colletotrichum truncatum*, a pathogen of hemp sesbania, is on deposit as NRRL #18134.

*Fusarium lateritium*, a pathogen of velvetleaf is on deposit as NRRL #12552.

The fungi were grown in liquid culture in suitable aqueous culture media for sufficient time to produce adequate fungal biomass to give effective compositions when incorporated in formulations of the present invention. Any growth medium in which the desired microorganisms will effectively grow can be used. One that is particularly useful consists of corn meal (15 g/L), soybean flour (15 g/L), sucrose (30 g/L), and calcium carbonate (3 g/L) made up to the desired volume with distilled or deionized water.

For example, the fungi were grown in 1-liter shake flask culture with the growth medium described above for seven days after inoculation, and homogenized in a commercial blender for about 30 sec., just prior to use. This fungal homogenate can be used as the source of the weed pathogenic fungus in formulations processed by the method of the present invention.

Alternatively, spores or other propagules of a fungal weed pathogen may be grown in liquid or solid culture, isolated, and used in the methods of the present invention.

Encapsulation of a fungal weed pathogen into a wheat gluten matrix is typically initiated by mixing wheat flour, filler and/or adjuvants, and aqueous fungal homogenate to form a cohesive and homogeneous dough. The order of combining the ingredients may be conducted in whatever way that facilitates the process. The quantity of wheat flour and the quantity of water that are mixed together must be sufficient to make a cohesive dough. Usually, a wheat flour:water ratio (by weight) of 1:0.4–0.8 is optimum, depending on the effects of other ingredients. The wheat flour component of a typical formulation is about 60–100% of the formulation ingredients other than water or fungus. The pH of the dough is usually in the range of 4–8. An effective amount of fungal biomass or fungal propagules must be incorporated in the dough. An "effective amount" is defined herein as that quantity of fungal ingredient which will achieve the desired level of weed control in use. The well-blended dough is rolled out into a sheet, dried, and broken up or ground into granules. The granules may be sieved to obtain the size range desired. Alternatively, before drying, the dough may be extruded or formed into special shapes such as thin strips or into pasta-like configurations familiar to the food industry.

The principal function of the wheat flour ingredient is to provide gluten to form dough and the matrix structure of the compositions of the present invention. However, the flour also serves as a nutrient source that may be beneficial to some types of fungi that are encapsulated in the dough.

Numerous inorganic and organic fillers such as clays, talc, vermiculite, peat moss, corn flour, rice flour, oat flour, soy flour, and cereal grain brans may be incorporated in formulations of this invention to reduce product costs and to confer improved properties. Kaolin, for example, may be added up to about 25% by weight of final product. Adjuvants such as gums, nutrients, pH modifiers, fungal spore germination promoters, weed infection promoters, humectants, weed tissue or extracts, and bactericides may be included in the formulations. Wheat gluten derived from wheat may be added to supplement the dough-forming protein content of wheat flour. The addition of materials to alter the density of the final products is also contemplated, including low density materials that would cause the products to float in water. A combination of two or more compatible weed pathogenic fungi, or a weed pathogenic fungus combined with other compatible biological or chemical pesticides, may be encapsulated, where feasible, to broaden the pesticidal properties of the products of this invention.

The method of this invention, including drying, should be carried out at temperatures that are safe for the entrapped living weed pathogenic fungi, typically below 40° C., and preferably at 15°–30° C. The dough sheet should be dried to about 9–13% water content. Grinding of the dried dough should be done under conditions that preserve the viability of the encapsulated fungus.

Granules or other product configurations produced by the method of this invention may be applied preemergence or postemergence to an agricultural field or to an environment with aquatic weeds. "Agricultural field" is defined to mean any terrestrial area where weed control is desired. When a pesticidally-effective amount of the granules are exposed to favorable environmental conditions of moisture, light, temperature, etc., the encapsulated fungus will proliferate and grow on the granule surface, inoculate the area of application with the fungus, and control the target weed. A "pesticidally-effective" amount is defined to mean that quantity of product which will result in a significant level of weed damage as compared to an untreated group. The actual amount may vary with the particular weed pathogen, the maturity and susceptibility of the target weed, and various environmental conditions.

In an alternative embodiment of the invention, the dried dough may be ground into particles fine enough to be suspended in a sprayable liquid and applied to soil or to the target weeds by spraying.

Distinct from a direct weed control application, products of this invention may also be used for the solid state culture and mass production of spores or other propagules of the encapsulated fungus. Products of this invention may also be used to inoculate an agricultural environment with a weed pathogenic fungus for purposes other than weed control.

In some instances, it may be advantageous to sterilize the wheat flour, water, and other ingredients used in the practice of this invention prior to addition of the biocontrol fungus to be encapsulated. However, in the case of the wheat flour, excessive heat can denature gluten proteins and reduce or eliminate their dough-forming properties which are central to the method of this invention. Therefore, sterilization procedures performed below about 50° C., such as by the use of ethylene or propylene oxide, are preferred.

The following examples are intended only to further illustrate the invention and are not intended to limit the scope of the invention.

EXAMPLE 1

*Alternaria cassiae* was grown in 1-L shake flask culture in a medium containing corn meal, soy flour, sucrose, calcium carbonate, and distilled water. An actively growing culture, seven days old, was homogenized for about 30 sec in a commercial blender immediately prior to use. This culture material is referred to herein as "aqueous fungal homogenate."

A 52-mL quantity of aqueous fungal homogenate was added to a mixture of 80 g semolina and 20 g of kaolin (type RC-32, Thiele Kaolin Co., Wrens, Ga., U.S.A.)

and mixed and kneaded by hand to form a cohesive dough. The dough was rolled out using a pasta maker to a sheet about 3 mm thick. The pH of the dough was 6.4. The dough sheet was folded twice and rolled out again. Folding and rolling were repeated about six times until the dough sheet was of homogeneous composition, then it was rolled a final time to a thickness of about 1.5 mm and set on a piece of window screen suspended so that the dough could air dry from the bottom as well as from the top. The dough sheet was dried at about 22° C. and 55-70% relative humidity to a final moisture content of about 10.5%. The dried dough sheet weighed 100.5 g. The dried dough sheet with encapsulated living fungal weed pathogen was ground using a table top, hand-operated grinder, then the granules were sieved to obtain the final products. The granules contained *Alternaria cassiae* dispersed throughout the granule matrix. The fungus grew on the granule surface when sufficient light and moisture were provided.

In order to evaluate and demonstrate the weed control efficacy of these products, granules were bioassayed against the target weed. To each of 12 pots, each pot containing three sicklepod seedlings, was added 1.0 g of granules with entrapped *Alternaria cassiae*. The granules were applied directly onto damp soil in each pot. The pots were placed in a dew chamber and provided with about a 12 hr dew period, then the pots were placed in a greenhouse. A total of three replicates of the experiment was conducted. After seven days, the percent infection and death of the weeds caused by application of the products of this invention were determined, and the results from the three replicates were averaged and reported in Table 1, samples 1-3. The use of the products of this invention caused considerable infection and death of the target weed, sicklepod (*Cassia obtusifolia* L.).

EXAMPLE 2

*Alternaia crassa* was grown, entrapped in granules, and the granules were evaluated as described in Example 1, except that the target weed was jimsonweed. Results are reported in Table 1, samples 4-5. The fungus grew on the granule surface when sufficient light and moisture were provided. The use of these products caused considerable infection and death of jimsonweed (*Datura stramonium* L.).

EXAMPLE 3

A 2-g quantity of *Alternaria crassa* spores [obtained as described in C. D. Boyette, Plant Science 45:223-228 (1986)] was blended with 80 g of semolina and 18 g of kaolin, then 52 mL of deionized water was added and mixed to form a cohesive dough which was further processed as described in Example 1 to make granules containing spores of *A. crassa* encapsulated throughout the granular matrix. The fungus grew on the granule surface when sufficient light and moisture were provided. These granules were evaluated as described in Example 1 against jimsonweed. Results are reported in Table 1, samples 6-7. Use of these granules led to considerable infection and death of the target weed, jimsonweed.

EXAMPLE 4

*Colletotrichum truncatum* was grown and entrapped in granules as described in Example 1, except that the target weed was hemp sesbania. Results are reported in Table 1, samples 8-10. Use of these products led to considerable infection and death of hemp sesbania (*Sesbania exaltata*). The fungus grew on the granule surface when sufficient light and moisture were provided.

EXAMPLE 5

*Fusarium lateritium*, a pathogen of the weed velvetleaf, was grown and incorporated into granules which were then evaluated as described in Example 1 except that the weed was velvetleaf. Results are reported in Table 1, samples 11-13. Use of these products led to considerable infection and death of velvetleaf (*Abutilon theophrasti* Medik.). The fungus grew on the granule surface when sufficient light and moisture were provided.

EXAMPLE 6

*Colletotrichum truncatum* was grown and encapsulated in granules as described in Example 1. Granules that were finer than 30 mesh were suspended in distilled water and sprayed onto hemp sesbania, and led to considerable infection and death of this weed.

It is understood that the foregoing detailed description is given merely by way of illustration and that modifications and variations may be made therein without departing from the spirit and scope of the invention.

TABLE 1

| Sample | Fungal pathogen | Granule size (mesh) | Target weed | Efficacy of treatment[1] % Weed infection | % Weed mortality |
|---|---|---|---|---|---|
| 1 | *Alternaria cassiae*[2] | 14-18 | sicklepod | 75 | 68 |
| 2 | " | 18-30 | " | 72 | 70 |
| 3 | " | >30 | " | 45 | 40 |
| 4 | *Alternaria crassa*[2] | 14-18 | jimsonweed | 82 | 82 |
| 5 | " | 18-30 | " | 75 | 70 |
| 6 | *Alternaria crassa*[3] | 14-18 | " | 90 | 85 |
| 7 | " | >30 | " | 46 | 25 |
| 8 | *Colletotrichum truncatum*[4] | 14-18 | hemp sesbania | 100 | 100 |
| 9 | " | 18-30 | " | 87 | 78 |
| 10 | " | >30 | " | 48 | 40 |
| 11 | *Fusarium lateritium*[2] | 14-18 | velvetleaf | 35 | 30 |
| 13 | " | 18-30 | " | 22 | 28 |

TABLE 1-continued

| Sample | Fungal pathogen | Granule size (mesh) | Target weed | Efficacy of treatment[1] | |
| --- | --- | --- | --- | --- | --- |
| | | | | % Weed infection | % Weed mortality |
| 16 | " | >30 | " | 12 | 5 |

[1]One g of granules/pot, 12 hr dew, rated on 7th day, avg. of 3 replications.
[2]Incorporated in dough as homogenized fungal mycelium.
[3]Incorporated in dough as fungal spores.
[4]Incorporated in dough as homogenized fungal mycelium and spores.

We claim:

1. A method for the encapsulation of weed pathogenic fungi comprising the steps:
   (a) mixing an effective amount of a weed pathogenic fungus with wheat flour and water to prepare a cohesive dough which entraps said fungus;
   (b) rolling out, extruding, or shaping said dough;
   (c) drying said dough to form a product that contains a weed pathogenic fungus encapsulated in a wheat gluten matrix.

2. The method of claim 1 including the addition of a filler material to said mixture of fungus, wheat flour, and water.

3. The method of claim 1 including the additional step of grinding the product of step (c) into granules or fine particles that contain encapsulated weed pathogenic fungi.

4. The method of claim 1 wherein said wheat flour is semolina made from durum wheat.

5. The method of claim 1 wherein said sufficient amount of fungus of step (a) was added in the form of homogenized mycelium and/or spores.

6. The method of claim 1 wherein said sufficient amount of fungus was mixed with a mixture of semolina and kaolin.

7. The method of claim 1 wherein said weed pathogenic fungus is at least one member selected from the group consisting of *Alternaria cassiae, Alternaria crassa, Colletotrichum truncatum,* and *Fusarium lateritium.*

8. A wheat gluten matrix product containing encapsulated weed pathogenic fungi produced by the method of either claim 1, 2, 3, 4, 5, 6, or 7.

9. The product of claim 8 in the form of dry, free-flowing granules.

10. The product of claim 8 in the form of dry, free-flowing particles fine enough to be suspended in a sprayable liquid.

11. A method for controlling weeds comprising the application of products containing a weed pathogenic fungus encapsulated in a wheat gluten matrix.

12. The method of claim 11 wherein products containing *Alternaria cassiae* are applied to control sicklepod.

13. The method of claim 11 wherein products containing *Alternaria crassa* are applied to control jimsonweed.

14. The method of claim 11 wherein products containing *Colletotrichum truncatum* are applied to control hemp sesbania.

15. The method of claim 11 wherein products containing *Fusarium lateritium* are used to control velvetleaf.

16. The method of claim 11 wherein said products are granules and are applied to soil.

17. The method of claim 11 wherein said products are fine particles that may be suspended in a sprayable liquid and applied by spraying to soil or to the target weed.

* * * * *